US007621903B2

(12) United States Patent
DeLegge

(10) Patent No.: US 7,621,903 B2
(45) Date of Patent: Nov. 24, 2009

(54) ANCHOR FOR IMPLANTED DEVICES AND METHOD OF USING SAME

(76) Inventor: Rebecca DeLegge, 3233 Cotton Field Dr., Mt. Pleasant, SC (US) 29466

(*) Notice: Subject to any disclaimer, the term of this patent is extended or adjusted under 35 U.S.C. 154(b) by 1108 days.

(21) Appl. No.: 10/706,453

(22) Filed: Nov. 12, 2003

(65) Prior Publication Data

US 2004/0116894 A1 Jun. 17, 2004

Related U.S. Application Data

(60) Provisional application No. 60/425,565, filed on Nov. 12, 2002.

(51) Int. Cl.
*A61M 31/00* (2006.01)

(52) U.S. Cl. .................................................... 604/508

(58) Field of Classification Search ............. 604/96.01, 604/97.01, 97.02, 104, 105, 106, 174, 178, 604/523, 192–194

See application file for complete search history.

(56) References Cited

U.S. PATENT DOCUMENTS 3,633,586 A * 1/1972 Sheridan ................ 128/207.15
4,666,433 A * 5/1987 Parks ......................... 604/178
5,071,405 A * 12/1991 Piontek et al. ......... 604/103.03
5,192,314 A * 3/1993 Daskalakis ................. 623/3.21
5,234,454 A * 8/1993 Bangs ........................ 606/191
5,411,475 A * 5/1995 Atala et al. .............. 604/96.01
5,888,220 A 3/1999 Felt et al.
6,306,177 B1 10/2001 Felt et al.
6,365,664 B1 * 4/2002 Eknoian ..................... 524/501
6,443,988 B2 9/2002 Felt et al.
7,105,116 B2 * 9/2006 Bellin et al. ................ 264/131

* cited by examiner

*Primary Examiner*—Manuel A Mendez
(74) *Attorney, Agent, or Firm*—B. Craig Killough

(57) ABSTRACT

A balloon is inflated with a flowable material that is semi-solid, or sets and becomes solid after it has entered the balloon. The flowable material is injected into the balloon through the balloon port, enters the balloon, and inflates the balloon. The viscosity of the material, or the solid nature of the material after it sets and solidifies, provides a lower anchor for a device that extends percutaneously into the body, such as a feeding tube.

9 Claims, 3 Drawing Sheets

14
10
6
16
2
18

12
8
4

6
10
16
2

18
20
22
12
8

14
16
2

12
8

ANCHOR FOR IMPLANTED DEVICES AND METHOD OF USING SAME

This application claims priority of provisional application Ser. No. 60/425,565 filed Nov. 12, 2002.

FIELD OF THE INVENTION

This invention relates to articles that are medically positioned or implanted in the body, and is more specifically directed to a device for anchoring devices including tubes or anchors that are positioned percutaneously, such as feeding tubes that extend through the abdominal wall into the stomach, and methods of installing and using same.

BACKGROUND OF THE INVENTION

Feeding tubes, tissue expanders and peristomal drains are examples of devices that are positioned in the body for medical purposes. These devices may be installed percutaneously, and must be anchored so that they are not pulled out in an unintended manner.

In particular, feeding tubes are used to supply nutrients directly to the stomach. One type of feeding tube is inserted through a stoma in the abdominal wall and extends into the stomach. The stomach communicates with the food source by means of the feeding tube, with food traveling from the food source through the feeding tube and directly into the stomach. Feeding tubes are used for patients who do not have proper motor control to permit ingestion of food through the esophagus, or cannot otherwise ingest food through the mouth and esophagus. Such patients include stroke victims who do have the ability to swallow food.

After the feeding tube is inserted through the abdominal wall and into the stomach, the tube must be secured, or anchored. In the prior art, a feeding tube has a balloon on one end, and an external bolster positioned along the length of the tube. The balloon communicates with a balloon port on the device that allows air or liquids to be placed into the balloon, to expand the balloon. The tube that communicates with the balloon has an opening or port to which a syringe may be fitted for injecting air or liquid material into the balloon. The balloon is expanded by the injected air or liquid material, and as the balloon expands within the stomach, the balloon provides retention means and keeps the tube from pulling out of the stomach. The bolster is positioned against the exterior of the gastric wall and against the patient's skin. The external bolster prevents the tube from being further inserted through the stoma and into the stomach. The bolster and the balloon act together to position and hold the feeding tube, with the outlet of the feeding tube present within the stomach.

The balloon of the prior art device presents problems. The balloon typically lasts from one week to three months. The balloon may break due to compression by the patient's movements, such as the patient simply sitting up. Preexisting small holes in the balloon may release fluids into the stomach. In some patients, the balloon breaks due to hyperacidic stomach content, resulting in an erosion and breakage of the balloon. Once the balloon breaks, the feeding tube may fall out of the stomach in the patient's bed, a condition that may go unnoticed for an extended period.

Once the balloon falls out, a replacement tube needs to be positioned within twelve to twenty-four hours, or the stoma begins to close. If the stoma tract closes, a more significant procedure must be performed, such as an endoscopic procedure to replace the tube with a percutaneous endoscopic gastronomy tube (PEG). Ultimately, a balloon feeding tube replaces the PEG tube and the cycle begins again. In short, balloon feeding tubes rupture unpredictably and prematurely, undesirably leaving the patient's stomach tract free to close.

SUMMARY OF THE PRESENT INVENTION

In the present invention, the balloon is inflated with a flowable material that is semi-solid, or sets and becomes solid after it has entered the balloon. The flowable material is injected into the balloon, through the balloon port, and enters the balloon. The material inflates the balloon to provide a lower anchor for a device that extends percutaneously into the body, or is a conduit into the body, such as a feeding tube, or which otherwise needs to be anchored within a cavity of the body.

DETAILED DESCRIPTION OF THE PREFERRED EMBODIMENT

Figure 1:
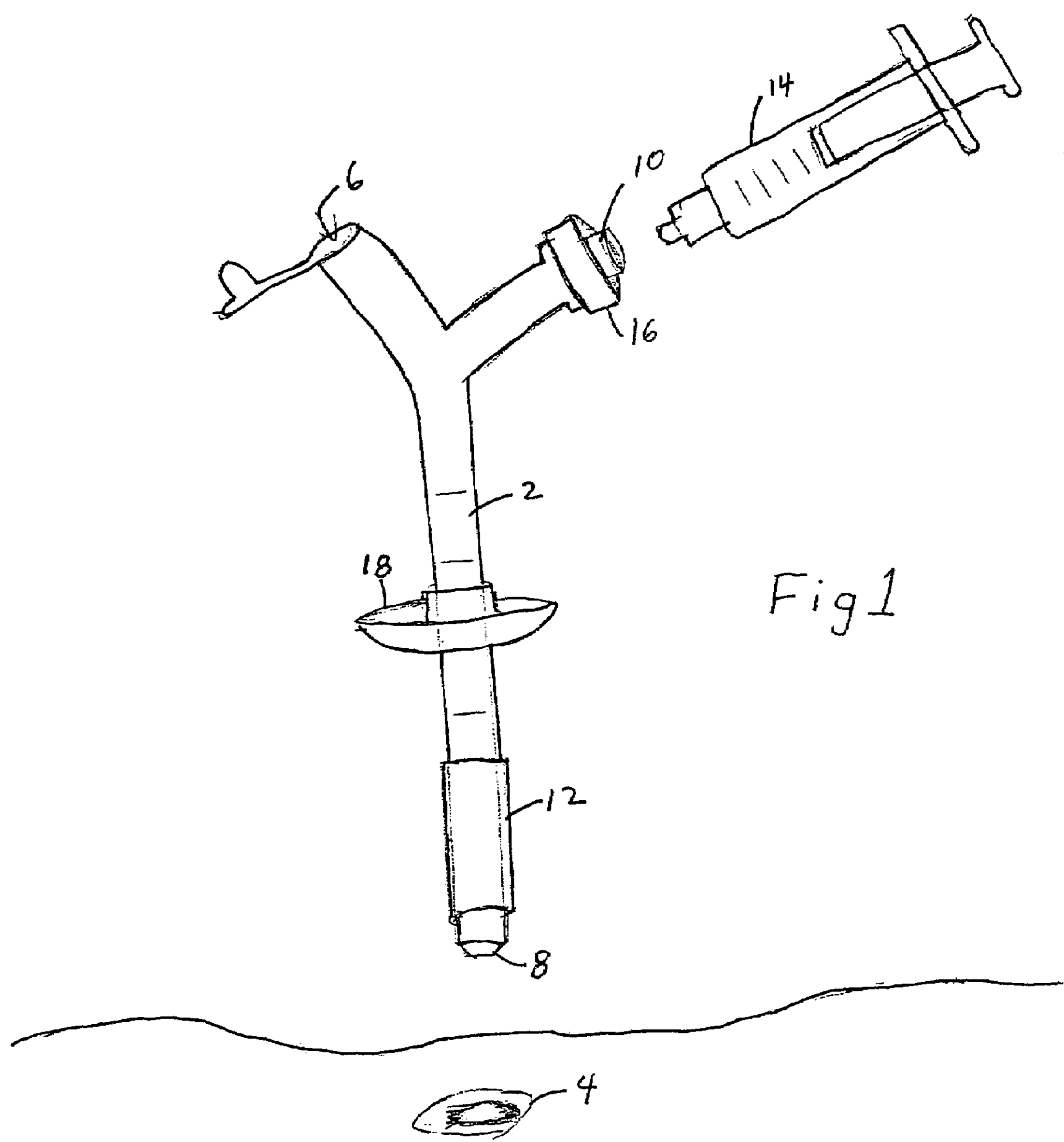
FIG. 1 shows a feeding tube that is used with the invention, with the feeding tube positioned over a stoma site.

Referring now the drawing figures, FIG. 1 shows a feeding tube 2 positioned over an existing stoma site 4. The tube has a feed port 6 that communicates with a feeding pump on one end, and an outlet 8 on an opposite end. The device has a balloon port 10 that communicates with the balloon 12 for inflating the balloon. Inflation may be accomplished by a syringe 14 that injects flowable material into the balloon. Other means for forcing the flowable material into the balloon may be used. A one-way valve 16 is incorporated into the balloon port to prevent material that is injected into the balloon port from exiting the balloon port. Near the outlet of feeding port is balloon 12, which is shown in FIG. 1 in a deflated condition. An external bolster 18 is present on the feeding tube.

A "balloon" is any container having expandable properties that are sufficient to receive and contain the flowable material as described herein. Further, the container or balloon is contracted to permit insertion, but must expand sufficiently, after inflation with the flowable material transported into it, to provide a barrier that will retain the feeding tube within the stomach.

Figure 2:
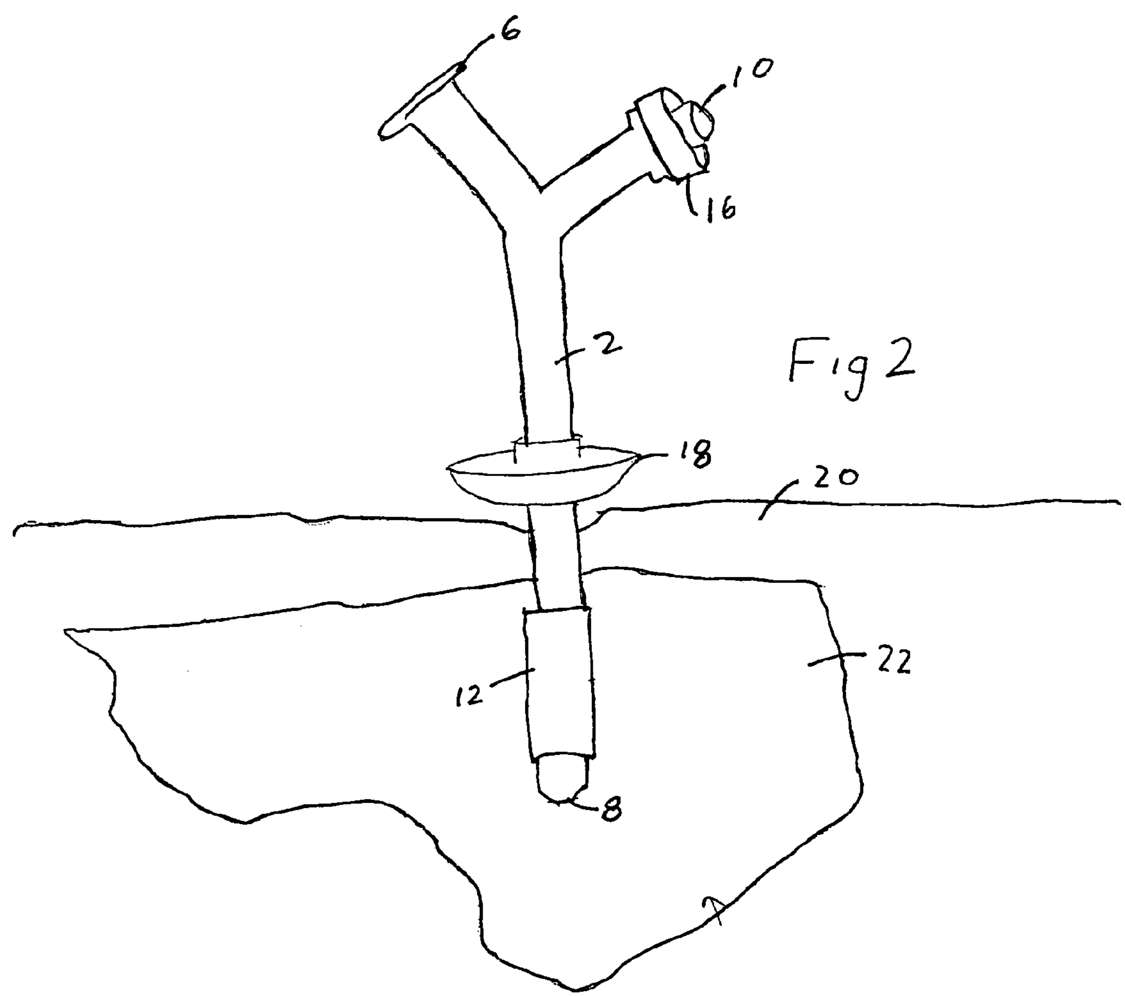
FIG. 2 shows the feeding tube inserted through the gastric wall, and into the stomach, prior to inflation of the balloon.

With the balloon deflated, the feeding tube may be inserted through the stoma site, through the gastric wall 20, and into the stomach 22. FIG. 2. The external bolster that abuts the patient's skin arrests the travel of the feeding tube through the gastric wall. The outlet of the feeding tube is now present within the stomach as desired, but in the position shown in FIG. 2, there is nothing to retain the feeding tube within the stomach, and the feeding tube is subject to being pulled from the stomach either inadvertently, or by a hostile patient.

Figure 3:
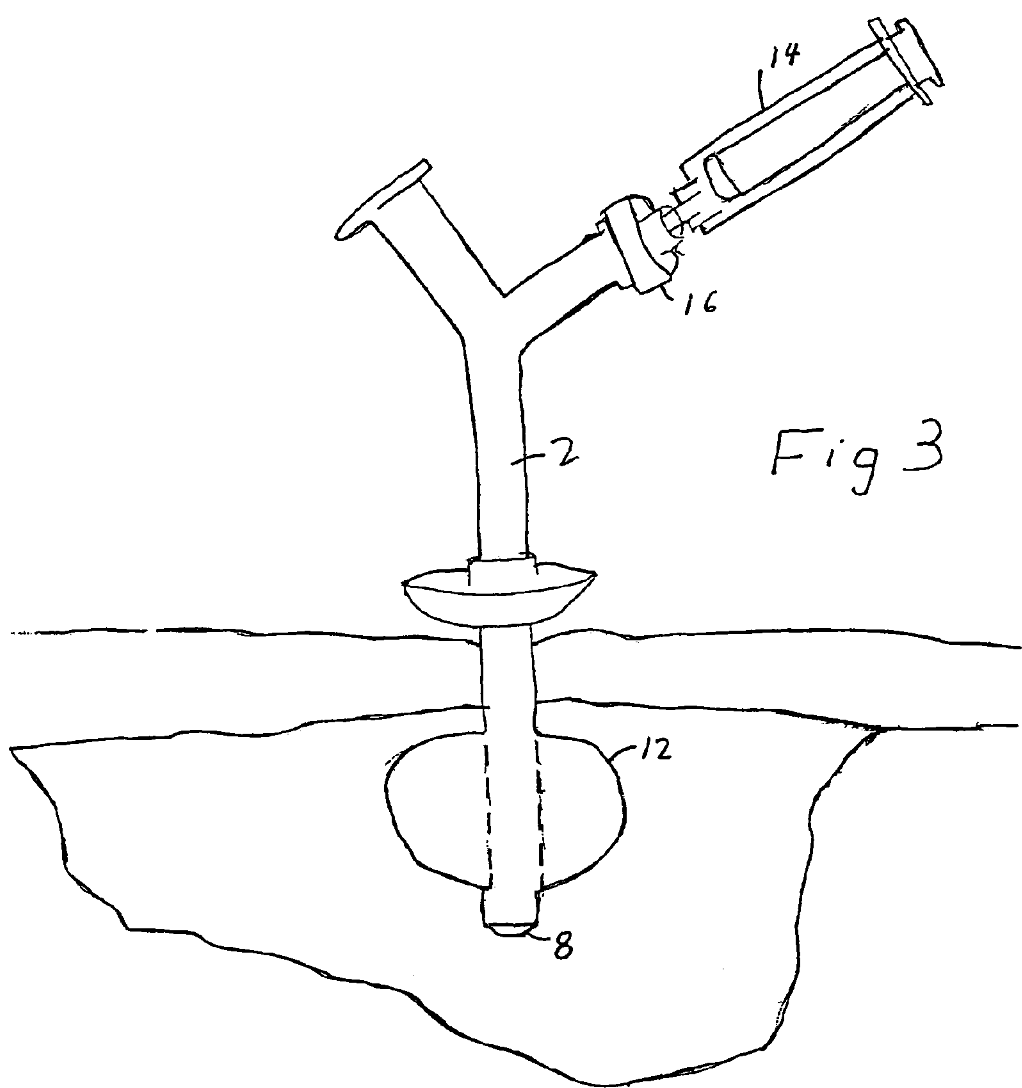
FIG. 3 shows the feeding tube in position with the balloon inflated, and the external bolster positioned.

As shown in FIG. 3, the balloon is inflated by inserting an inflation material through the balloon to a port. In the preferred embodiment, a syringe is affixed to the balloon port, and the inflation material is transported under pressure through the balloon port and into the balloon to inflate the balloon. In the inflated position, the balloon retains the feeding tube within the stomach by resisting forces that will tend to withdraw the feed tube from the stomach.

In the present invention, the syringe 14 is filled with a flowable material that will set after it has entered the balloon. The syringe is fitted to the balloon port, whereupon the flowable material is expelled from the syringe and forced under pressure into the balloon. This procedure is repeated until the balloon is filled to the desired level. After the flowable material sets, it provides a solid anchor that is not subject to being removed by breakage of the balloon, or by deformation of the balloon.

The flowable material may be a material that will set and solidify at body temperatures by polymerization of the material. Typically, two or more components that will form the polymer are mixed immediately before or immediately after the feeding tube is inserted to the stomach. The flowable material that will form a polymer is mixed, and inserted by means of the syringe as described to inflate the balloon. The material then polymerizes and sets, so that an anchor for the feeding tube is formed within the stomach. It is preferred that the polymer material solidifies and sets within approximately five minutes from mixing to use. Other flowable materials that will solidify at body temperatures, while providing sufficient time to prepare the material and inject it into the balloon, may be used.

Alternatively, the flowable material may be a semi solid material that will flow into the balloon under pressure so as to inflate the balloon. The semi solid material does not set to a solid form, but has sufficient viscosity to retain the balloon within the stomach.

The flowable material should be inert. One example of a material that may be used is an anti-microbial alginate.

The balloon acts as a mold that shapes or forms the flowable material prior to the material setting. Once the material has set, the balloon is no longer needed to assist in anchoring the feeding tube. Prior, or subsequent, damage, defects, or deformation of the balloon will not prevent the device from holding the feeding tube in place. Accordingly, the useful life of the feeding tube according to the invention described herein is superior to prior art devices and processes wherein the balloon is filled with air or liquids that will escape from the balloon if it is punctured or improperly deformed.

What is claimed is:

1. A method of anchoring a feeding tube, comprising the steps of:

a) inserting a feeding tube into a stomach, wherein said feeding tube comprises an inflatable container, and wherein said inflatable container is positioned inside a gastric wall;

b) inflating said inflatable container after positioning said inflatable container inside the gastric wall by inserting a flowable material into said inflatable container, wherein said flowable material is a material that sets and becomes solid or semi-solid; and c) allowing said flowable material to set and form an anchor for said feeding tube after said flowable material is inserted into said inflatable container.

2. A method of anchoring a feeding tube as described in claim 1, wherein said feeding tube comprises a bolster that is positioned above said inflatable container, and wherein, after insertion of said feeding tube into said stomach, a gastric wall is between said bolster and said inflatable container.

3. A method of anchoring a feeding tube as described in claim 1, wherein said feeding tube comprises a port that is suitable for receiving a device for inserting said flowable material, and a feed port.

4. A method of anchoring a feeding tube as described in claim 3, wherein said port that is suitable for receiving a device for inserting said flowable material comprises a one way valve.

5. A method of anchoring a feeding tube as described in claim 1, wherein said flowable material is a polymer, and wherein said polymer sets to form a solid or a semisolid after said flowable material is inserted in said inflatable container.

6. A method of anchoring a feeding tube as described in claim 1, wherein said flowable material is a polymer.

7. A method of anchoring a feeding tube as described in claim 1, wherein said flowable material comprises a first part and a second part, and wherein said first part and said second part combine and set to form as a solid or a semisolid after said flowable material is inserted in said inflatable container.

8. A method of anchoring a feeding tube as described in claim 1, wherein said flowable material comprises an antimicrobial agent.

9. A method of anchoring a feeding tube as described in claim 1, wherein said flowable material sets to form a solid.

* * * * *